United States Patent
Miller

(10) Patent No.: US 7,122,376 B2
(45) Date of Patent: *Oct. 17, 2006

(54) CALIBRATION STANDARDS, METHODS, AND KITS FOR WATER DETERMINATION

(75) Inventor: Scott Andrew Miller, Beech Grove, IN (US)

(73) Assignee: Facet Analytical Services and Technology, LLC, Beech Grove, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/399,117

(22) PCT Filed: Nov. 1, 2001

(86) PCT No.: PCT/US01/27790

§ 371 (c)(1),
(2), (4) Date: Apr. 14, 2003

(87) PCT Pub. No.: WO02/40991

PCT Pub. Date: May 23, 2002

(65) Prior Publication Data

US 2004/0110298 A1   Jun. 10, 2004

(51) Int. Cl.
*G01N 33/18* (2006.01)

(52) U.S. Cl. .............. 436/42; 436/8; 436/19; 436/39

(58) Field of Classification Search .......... 422/61; 436/39, 42, 8, 19
See application file for complete search history.

(56) References Cited

U.S. PATENT DOCUMENTS

| | | | |
|---|---|---|---|
| 4,035,359 A | 7/1977 | Christensen et al. | |
| 4,071,529 A | 1/1978 | Christensen et al. | |
| 4,104,190 A * | 8/1978 | Hartshorn | 252/187.21 |
| 4,143,129 A | 3/1979 | Marsdea | |
| 4,154,845 A | 5/1979 | Christensen et al. | |
| 4,219,435 A * | 8/1980 | Biard et al. | 510/439 |
| 4,631,305 A * | 12/1986 | Guyer et al. | 523/400 |
| 4,684,650 A | 8/1987 | Bogeso | |
| 4,818,325 A | 4/1989 | Hiraiwa et al. | |
| 4,933,453 A | 6/1990 | Hrib et al. | |
| 5,037,984 A | 8/1991 | Hrib et al. | |
| 5,136,037 A | 8/1992 | Hrib et al. | |
| 5,229,388 A | 7/1993 | Hrib et al. | |
| 5,288,507 A | 2/1994 | Sims et al. | |
| 5,292,364 A | 3/1994 | Hiraiwa et al. | |
| 5,340,541 A | 8/1994 | Jackson et al. | |
| 5,371,087 A | 12/1994 | Hrib et al. | |
| 5,401,744 A | 3/1995 | Behme | |
| 5,476,874 A | 12/1995 | Hungate et al. | |
| 5,567,910 A | 10/1996 | Chattopadhyay | |
| 5,612,217 A | 3/1997 | Shafiee et al. | |
| 5,616,344 A * | 4/1997 | Battist et al. | 424/486 |
| 5,646,148 A | 7/1997 | Huff et al. | |
| 5,654,003 A * | 8/1997 | Fuisz et al. | 424/469 |
| 5,674,854 A | 10/1997 | Bodley et al. | |
| 5,747,540 A | 5/1998 | Coburn et al. | |
| 5,801,186 A | 9/1998 | Hrib et al. | |
| 5,807,841 A | 9/1998 | Huff et al. | |
| 5,817,609 A | 10/1998 | He et al. | |
| 5,830,500 A * | 11/1998 | El-Rashidy et al. | 424/465 |
| 5,854,226 A | 12/1998 | Penkler et al. | |
| 5,994,281 A | 11/1999 | He et al. | |
| 6,010,719 A * | 1/2000 | Remon et al. | 424/464 |
| 6,071,916 A | 6/2000 | Askin et al. | |
| 6,074,998 A | 6/2000 | He et al. | |
| 6,131,442 A * | 10/2000 | Krause | 73/73 |
| 6,180,634 B1 | 1/2001 | Vacca et al. | |
| 6,245,917 B1 | 6/2001 | Bosch et al. | |
| 6,284,775 B1 | 9/2001 | Hrib et al. | |
| 6,432,952 B1 | 8/2002 | Crocker et al. | |
| 6,503,927 B1 | 1/2003 | Ronsen et al. | |
| 6,509,347 B1 | 1/2003 | Xu et al. | |
| 6,620,791 B1 | 9/2003 | Cooper et al. | |
| 6,642,237 B1 | 11/2003 | Tata et al. | |
| 6,667,299 B1 | 12/2003 | Ahlem et al. | |
| 2002/0056206 A1 | 5/2002 | Pace et al. | |
| 2002/0058065 A1 | 5/2002 | Guivarc'h et al. | |
| 2002/0182723 A1 | 12/2002 | Zhang et al. | |
| 2002/0188001 A1 | 12/2002 | Xu et al. | |
| 2003/0060425 A1 | 3/2003 | Ahlem et al. | |
| 2003/0083231 A1 | 5/2003 | Ahlem et al. | |
| 2003/0125336 A1 | 7/2003 | Fleitz et al. | |
| 2003/0166702 A1 | 9/2003 | Kor et al. | |

FOREIGN PATENT DOCUMENTS

| | | |
|---|---|---|
| EP | 0 482 465 A | 4/1992 |
| JP | 04297869 A2 | 10/1992 |

(Continued)

OTHER PUBLICATIONS

Hawley. The Condensed Chemical Dictionary, tenth edition, 1981, p. 953.*

(Continued)

*Primary Examiner*—Maureen M. Wallenhorst
(74) *Attorney, Agent, or Firm*—Woodard, Emhardt, Moriarty, McNett & Henry LLP

(57) ABSTRACT

The invention relates to a formed tablet calibration standard-reagent for calibrating Karl Fischer reactions for determining water content in a substance, the reagent containing a first component, namely sodium tartrate dihydrate, and a second component, namely magnesium stearate. The invention further relates to a method for determining the water content of a substance using a Karl Fischer analysis. The invention further relates to a formed tablet calibration standard-reagent kit that includes a sealed package containing a formed tablet calibration standard-reagent for a Karl Fischer reaction.

7 Claims, No Drawings

FOREIGN PATENT DOCUMENTS

WO  WO 02/040991 A2  5/2002

OTHER PUBLICATIONS

Neuss J D et al: Sodium Tartrate Dihydrate as a Primary Standard for Karl Fischer Reagent: Analytical Chemistry, American Chemical Society, Columbus, US, vol. 23, 1951, pp. 1332-1333, XP001042005 ISSN: 0003-2700 the whole document.

Ohm A: "Interaction of Bay t 3839 coprecipitates with insoluble excipients" European Journal of Pharmaceutics and Biopharmaceutics, Elsevier Science Publishers B.V., Amsterdam, NL, vol. 49, No. 2, Mar. 1, 2000, pp. 183-189, XP004257154 ISSN: 0939-6411 p. 186, left-hand column—p. 188, Left-hand column.

Burger A et al: "Polymorphism and preformulation studies of lifibrol" European Journa. of Pharmaceutics and Biopharmaceutics, Elsevier Science Publishers B.V., Amsterdam, NL, vol. 49, No. 1, Jan. 3, 2000, pp. 65-72, XP004257136 ISSN: 0939-6411 p. 66, right-hand column, paragraph 1.

\* cited by examiner

CALIBRATION STANDARDS, METHODS, AND KITS FOR WATER DETERMINATION

BACKGROUND OF THE INVENTION

This invention relates to improved calibration reagents for water determination using the Karl Fischer reaction. More particularly, the invention relates to a formed tablet calibration standard-reagent for calibrating Karl Fischer reactions for determining water content in a substance, said reagent containing a first component, namely sodium tartrate dihydrate, and a second component, namely magnesium stearate.

Moisture measurement is valuable because the presence of water can adversely affect a variety of applications across multiple industries. Some examples include pharmaceutical drug stability; foodstuff storage quality; properties of oils (e.g. viscosity); and reduced chemical reaction yield (e.g. production of plastics). Moisture content determination is an evaluation criterion necessary for stability considerations of New Drug Applications. Accurate control and monitoring of moisture in these fields is often required by regulatory agencies and necessary to improve product quality.

A number of chromatographic, spectroscopic, electronic, thermal, and wet chemical methods have been used in the past to determine moisture levels (S. K. MacLeod, Anal. Chem., 1991, 63, 557A–565A). The most common of these are loss on drying (LOD), thermogravimetric analysis (TGA), gas chromatography using a thermal conductivity detector, and the Karl Fischer titration. Of these most common water content measurements, however, the Karl Fischer titration has become the method of choice and is now the approach most widely used in the determination of water content. The determination of moisture in materials such as liquids and solids by the Karl Fischer reaction is well known and widely used since it was first described by Karl Fischer in Angewandte Chemie 48, pages 394–396 (1935). Numerous publications have also described this technique for water determination, and reference is made to a general text by J. Mitchell, Jr. and D. M. Smith, entitled "Aquametry", published by John Wiley and Sons, 1980. Reference is also made to a publication by E. Scholz entitled, "Karl Fischer Titration," published by Springer Verlag in 1984.

In a Karl Fischer reaction, the water to be determined reacts with iodine on a quantitative basis and consequently, the amount of reacted iodine is a measure of the amount of water present in the sample. The reaction proceeds according to the following expression:

$$H_2O + SO_2 + I_2 = 2H^+ + 2I^- + SO_3 \quad (1)$$

The titration can be run in either protic or aprotic medium, with the protic medium seeing wider use due to higher sensitivity of the titer to sample and solvent composition (M. S. Kamat, R. A. Lodder and P. P. DeLuca, Pharmaceutical Research, 1989 6(11) 961–965.). The reaction in protic media (i.e., alcohol) involves sulfur dioxide reacting with the alcohol to produce an alkyl sulfite in a buffered medium using an appropriate base to maintain the solution at the optimal pH. In a coulometric experiment, the iodine is generated electrically from iodine present in the cell. The electric efficiency of this method is generally 100%, and the amount of water in the sample is calculated from the number of moles of electrons used in the iodine generation. The components necessary to carry out this reaction have been formulated and are readily available as Karl Fischer reagents. These reagents are divided into two groups, single-component and two-component systems. In the single-component systems, all ingredients (iodine, buffer, $SO_2$, and solvent) are in one solution. In the two-component systems, the "vessel" solution contains the buffer, $SO_2$, and a solvent, while the "titrant" solution contains iodine in a suitable solvent.

Thus, Karl Fischer reagents are used in several types of analysis. A volumetric analysis using a volumetric reagent determines moisture by measuring the volume of the Karl Fischer reagent consumed during the analysis. A coulometric analysis using a coulometric reagent generates iodine by passing a current through the reagent and determines the moisture from the amount of current.

Analytical instrumentation, semi-automating the Karl Fischer assay, is most commonly used to conduct Karl Fischer titrations. Working medium (Methanol) is added to the titration vessel and conditioned to equilibrium (end point with a slight excess of reagent) with titrant. The weighed sample is then delivered into the vessel for titration to the same end point. The amount of water in the sample under test is determined using the reagent strength factor (based on instrument calibration with material of known water content) and the volume of reagent dispensed to reach equilibrium.

Examples, of instrumentation utilizing the Karl Fischer reaction for determination of water content comprise: 1) Volumetric Moisture Meter, Model KF-100, Mitsubishi Chemical Corporation; 2) Aquastar® Volumetric Titrator, Models V1B and V-200, EM Science; 3) Schott Titroline KF, Schott; 4) Metrohm® & Volumetric Karl Fischer Titration Systems, Models 701, 784, 758, 756, Brinkmann Instruments, Incorporated; 5) Orion® Volumetric Karl Fischer Titrators, Models TURB02™ and AF8, Thermo Orion, Incorporated; and 6) Mettler-Toledo Titrators, Models DL53, DL55, DL58, Mettler-Toledo Corporation.

Accurate moisture content determination measurements using the Karl Fischer titration are contingent on the proper working order of the titration instrument and the chemical reactions. Successful moisture content determinations require that 1) equipment be in proper working order, 2) reagents be stable and not depleted, 3) moisture be excluded from the system, 4) the anodic reaction produce 100% current yield, 5) the cathodic reaction does not interfere with the titration, and 6) the reaction not be adversely affected by the sample matrix.

To assure that these criteria are being met, the quality of the analysis is checked against calibration standards containing known moisture content. The correct moisture content determination for the standards confirms that the Karl Fischer titration analysis is running properly, or indicates that a problem exists. A variety of materials have been proposed as standards for moisture content determinations. The principal requirements of these materials are 1) that they contain a stoichiometric amount of moisture that is stable over a wide range of temperature and humidity, 2) solubility in the Karl Fischer titration reagents, 3) ease of handling and storage, 4) availability, and 5) uniformity (M. S. Kamat, R. A. Lodder and P. P. DeLuca, Pharmaceutical Research, 1989, 6(11), 961–965.).

Many possible calibration standards for Karl Fischer determination of water have been described. These include: purified water, certified water standards (known water content determined by assay), Aluminum potassium sulfate, Ammonium oxalate, Citric acid, Ferric ammonium sulfate, Ferrous ammonium sulfate, Lactose, Oxalic acid, Potassium citrate, Potassium sodium tartrate, Potassium tartrate, sodium acetate, sodium bitartrate, sodium citrate, and sulfosalicylic acid (Neuss, J. D. Obrien, and M. G. Frediani, H. A., Analytical Chemistry, 23, 1332 [1951]).

Much effort has been given to making liquid water standard solutions less hygroscopic. These efforts have not been completely successful, as the water content of the solutions change after the septum over the solutions has been pierced several times. Water is a very good calibration reagent, but it is difficult to accurately dispense liquid water into the Karl Fischer titrator. When delivered by volume, the inaccuracies of the small amount delivered make it difficult to obtain an accurate value. A more accurate measurement is obtained when the liquid water is delivered by weight, but this again presents difficulties in dispensing the water into the titrator. Also, degradation and stability of the standard become relevant due to the special material handling characteristics that must be considered for certified liquid calibration media.

Use of sodium tartrate dihydrate in powder form as a calibration standard for KF reactions is known in the art (E. Scholz, Karl Fischer Titration-Determination of Water-Chemical Laboratory Practice, Springer-Verlag, N.Y. 1984, T. H. Beasley, H. W. Siegler, R. L. Charles and P. King, Anal. Chem., 1972, 44, 1833–1840). However, bulk powder calibration standards are difficult to manipulate, which can result in increased assay variability due to the ingress of ambient moisture and the residual standard unaccounted for during sample addition. Another problem with the sample transfer process of the prior art is dispensing the calibration standard material into the Karl Fischer titrator. When trying to pour the powder material through a funnel into the titrator, some material is lost into the atmosphere or adheres to the sampling funnel, and thus is not all dispensed into the titrator. To mitigate this detriment, weighing paper can be rolled to create a funnel, but this requires operator dexterity. In either case, during the transfer of the powder, the titrator is open to the atmosphere, and the length of time the vessel is open is inversely related to the accuracy of the determination. Therefore, the prior art method using powder calibration standards requires significant analyst time and creates variability in assay results.

Thus, in its prior art configuration, Karl Fischer titrations were affected by: 1) sample transfer time, 2) relative humidity in the laboratory, and 3) material lost in the material transfer. These factors make it desirable to have an improved calibration standard reagent. Such an improved reagent would result in reduced time to load the reagent, provide for more accurate and quantitative transfer, and have less fluctuation in water content, as compared to the prior art liquid and powder calibration standards.

Accordingly, it is an object of this invention to provide a formed tablet calibration standard-reagent for calibrating Karl Fischer reactions for determining water content in a substance. It is another object of this invention to provide an improved process for the determination of water in a sample using the Karl Fischer reaction, in which the calibration reagent that is employed is a formed tablet calibration standard-reagent. Said formed tablet calibration standard-reagent containing a first component, namely sodium tartrate dihydrate, and a second component, namely magnesium stearate.

A formed tablet calibration standard-reagent would fundamentally reduce variability in the Karl Fischer assay. Differences due to analyst technique would be minimized because standard addition is simplified and more consistent. Cumbersome use of a syringe and injection into the titration vessel would be replaced with a single hand transfer of the tablet to the vessel through the sample port. Titration methodology would remain the same in all other aspects with the exception of instrument calibration. A formed tablet calibration standard would remove the barriers posed by prior art standards which act to deter the automation of Karl Fischer determination of water content. An automated Karl Fischer assay employing a formed tablet calibration standard would dramatically increase productivity in Karl Fischer water determinations.

These and other objects, features, and advantages will be apparent from the following more particular description of the preferred embodiments of the invention.

BRIEF SUMMARY OF THE INVENTION

The invention relates to a formed tablet calibration standard-reagent for calibrating Karl Fischer reactions for determining water content in a substance, said reagent containing a first component, namely sodium tartrate dihydrate, and a second component, namely magnesium stearate, where the ratio by percent weight of said first component to said second component is from 99.7:0.3 to 99:1.

The invention further relates to a method for determining the water content of a substance using a Karl Fischer analysis wherein, the reaction is calibrated using a calibration standard, the improvement comprising using said formed tablet calibration standard-reagent. The invention further relates to a formed tablet calibration standard-reagent kit, comprising a sealed package containing said formed tablet calibration standard-reagent.

DETAILED DESCRIPTION OF THE INVENTION

As used herein, "Karl Fischer reaction" refers to the chemical reaction described by equation (1) supra, and all of the embodiments of that reaction herein described including those that employ semi-automated instrumentation (described supra).

The tablets described herein for use in calibrating Karl Fischer reactions may be formed by the customary procedures in the art of tablet making. In preparation of these improved reagents, it is preferable that the ratio of said first component to said second component is from 99.7:0.3 to 99:1. Preferably, the ratio is 99.6:0.4, 99.5:0.5, and 99.4:0.6. Most preferably, the ratio is 99.5:0.5.

The tablet may have a total weight ranging from about 25 milligrams to 500 milligrams. Preferably, the total weight is from about 50 milligrams to 500 milligrams. Most preferably the total weight is about 200 milligrams.

Of all the possible calibration standard materials described above, sodium tartrate dihydrate was selected for preparation of the formed tablet calibration standard-reagent. Bulk sodium tartrate is nearly 100% pure and stable for an extended duration, without special storage requirements. In addition, sodium tartrate has a known theoretical moisture content. These advantages are incorporated into the tablet because of the formulation process. After size exclusion of larger crystals, the tartrate is compressed to the desired weight. The weight of the tablet determines its water content. This target amount is determined based on the optimum operating range of the titrator being used. When the water content of the replicate under test falls within this range, the variability in the assay is reduced. Since operating ranges vary by manufacturer, range appropriate sized tablets can be developed for optimal results in a specific instrument type.

The addition of magnesium stearate improved tablet robustness and eliminated capping. The development of tablet formulation included experimentation to assess compression and tablet hardness versus release of moisture in the Karl Fischer assay. Tablets were formulated with 0.25% magnesium stearate; however, tablet production failed. The lack of sufficient lubricant caused the press to seize during production. A preferred embodiment was determined to be tablet production with 0.5% magnesium stearate by weight. This will be explained in more detail by reference to the following examples, which are merely illustrative, and not limiting of the invention.

EXAMPLE

Sodium tartrate, dihydrate ACS reagent grade, was used as the starting material to make formed tablets. Crystals were sieved through a #30 mesh screen (Fischer Standard Testing Sieve, 600 micrometer opening), and placed in a common container. Retained material was discarded. To promote formation of the tablet, magnesium stearate was added to the filtered crystals by sizing through the same screen, and adding the excipient to the mixture. The two components, sodium tartrate and magnesium stearate, were mixed at a ratio of 99.5:0.5 percent by weight for 30 minutes using a "tumble" style mixing apparatus to achieve homogeneity.

The homogeneous mixture was then compressed into formed tablets using a common tablet press. A 7-millimeter round tool and die set was selected to form the tablets. Tablet production was carried out according to customary practices in the art. The tablets produced by this procedure were found to have an average thickness of 0.155–0.160 inches, and an average hardness of 1.3 KP.

The resulting tablets were surprisingly well formed and durable. In previous attempts to form tablets without magnesium stearate, or with 0.25% magnesium stearate, the tablets were not well formed and could not be handled without degradation of the tablets. The hardness of the tablet is known in the art of tablet making to be important to the structural and functional characteristics of the tablet. Further, it is known in the art of tablet making that generally the greater the force that is applied to the materials to be formed, the greater the hardness of the resulting tablet. Surprisingly, it was discovered that formation of the tablets of the present invention did not follow this relationship. Unexpectedly it was determined that the combination of sodium tartrate dihydrate with magnesium stearate in the ratio of 99.5:0.5 produced tablets of optimal hardness. Tablets formed of this ratio were subsequently determined in Karl Fischer water determination analysis to provide results that were closest to the theoretical water content of sodium tartrate dihydrate, and therefore are most preferable as a formed tablet calibration standard-reagent.

Surprisingly, the tablets formed with 0.5% magnesium stearate could be handled and used in the methods of Karl Fischer water determination described herein without crumbling and without the losses of material to the environment or upon contact with transferring instruments such forceps or weighing boats. The compact and discrete nature of the tablets minimized the handling requirements by the analyst, which resulted in less time to execute the analysis. The formed tablet calibration standard reagent was superior to the use of powder or liquid standard reagents in that analyst time was not required to aliquot the standard, and in that the transfer process was discrete and expedient.

Several experiments have been conducted to show that the formed tablet calibration standard-reagent of the present invention would produce values in Karl Fischer water determinations consistent with the expected theoretical value for sodium tartrate dihydrate. Consistency with the expected value is necessary in order for the tablet to be useful as a calibration standard reagent for Karl Fischer water determinations.

The formed tablet calibration standard-reagents prepared with 99.5% sodium tartrate dihydrate and 0.5% magnesium stearate were analyzed by Karl Fischer analysis. A commercial titration apparatus was used for the assays (Orion® Volumetric Karl Fischer Titrators, Models TURB02™). Each moisture analysis was conducted according to the customary procedures for this instrument. Briefly, the instrument is standardized by accurately weighing by difference approximately 30 mg of a liquid standard, namely Hydranal® water standard 10.0. The aliquot was delivered into the titration vessel and titrated to the end point with Karl Fischer reagent according to customary procedures. The tablets of Example 1 were then analyzed and water content was determined by customary procedure for this instrument. The empirical values observed were within 5 percent of the theoretical water content calculated for the sodium tartrate dihydrate tablets.

A preferred embodiment of the present invention pertains to the use of the formed tablet calibration standard-reagent for calibrating Karl Fischer wherein the Karl Fischer reaction employs the two-component reagent system described supra. Surprisingly, it was determined that the two-component system has a greater capacity for repeated analyses as compared to the one component system when using the formed tablet calibration standard-reagent.

The invention further relates to a method for determining the water content of a substance using a Karl Fischer analysis, wherein the reaction is calibrated using a calibration standard, the improvement comprising using a formed tablet calibration standard-reagent.

The formed tablet calibration standard-reagent is used to calibrate the Karl Fischer reaction for determining water content in test substances. In use, the formed tablet calibration standard-reagent replaces the prior art calibration standard in the method of calibrating the Karl Fischer reaction and determining the water content of test samples. Use of the tablet provides several advantages over the prior art standards, including reducing the time and effort required of the analyst and reducing the time the reaction vessel is open to the environment. Further, a formed tablet calibration standard-reagent removes the barriers posed by liquid and bulk-powder standards to complete automation of the assay. Material handling of samples in tablet form is easily manipulated by robotics. The formed tablet calibration standard-reagent simplifies the requirements for assay automation, and is particularly well suited for pharmaceutical applications where the samples for water content determination are often pills or tablets. This simplified automation strategy would replace repetitious, tedious, and variable manual determinations of moisture content.

The invention further relates to a formed tablet calibration standard-reagent kit, comprising a sealed package containing said formed tablet calibration standard-reagent. These new reagents can be employed in kits that are sold to users for the determination of water content. An example is a sealed package containing these new reagents, where the calibration tablet can be easily removed from the sealed package and introduced into the Karl-Fischer reaction vessel.

While the invention has been described with respect to particular embodiments thereof, it will be apparent to those of skill in the art that variations can be made therein without departing from the spirit and scope of the invention. The intended scope of the invention is to be limited only by the issued claims thereof.

I claim:

1. In a method for determining the water content of a substance using a Karl Fischer reaction, wherein the reaction is calibrated using a calibration standard, the improvement comprising calibrating the reaction with a formed tablet calibration standard-reagent, wherein the formed tablet calibration standard-reagent comprises a water-containing ingredient effective to interact with a Karl-Fischer reagent.

2. A method according to claim 1, wherein the formed tablet calibration standard-reagent is enclosed within a sealed package.

3. A method according to claim 1, wherein the formed tablet calibration standard-reagent comprises sodium tartrate dihydrate.

4. A method according to claim 1, wherein the formed tablet calibration standard-reagent comprises magnesium stearate.

5. A method according to claim 1, wherein the formed tablet calibration standard-reagent comprises a weight of between about 25 milligrams and 500 milligrams.

6. A method for calibrating a Karl Fischer reaction for determining a water content of a test substance, the method comprising calibrating the reaction with a formed tablet calibration standard-reagent, wherein the formed tablet calibration standard-reagent comprises a water-containing ingredient effective to interact with a Karl Fischer reagent.

7. A method according to claim 6, comprising:

providing an instrument to be used to perform the Karl Fischer reaction for determining the water content of the test substance; and conducting a calibrating Karl Fischer reaction in the instrument, the calibrating Karl Fischer reaction providing an empirical value for the water content of the formed tablet calibration standard-reagent.

* * * * *